US011235332B2

(12) United States Patent
Han et al.

(10) Patent No.: US 11,235,332 B2
(45) Date of Patent: Feb. 1, 2022

(54) ACCELERATED HYDROLYSIS SYSTEM

(71) Applicant: Ethicon, Inc., Somerville, NJ (US)

(72) Inventors: Yuxin Han, Bridgewater, NJ (US);
Yuewu Chen, Somerville, NJ (US);
Dechun Wu, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 634 days.

(21) Appl. No.: 16/008,201

(22) Filed: Jun. 14, 2018

(65) Prior Publication Data

US 2019/0381508 A1    Dec. 19, 2019

(51) Int. Cl.
| B01L 7/00 | (2006.01) |
| G01N 33/44 | (2006.01) |
| B01F 13/08 | (2006.01) |
| B01J 19/00 | (2006.01) |
| A61L 27/58 | (2006.01) |

(52) U.S. Cl.
CPC ............... B01L 7/52 (2013.01); B01F 13/08 (2013.01); B01J 19/0013 (2013.01); G01N 33/442 (2013.01); A61F 2210/0004 (2013.01); A61L 27/58 (2013.01)

(58) Field of Classification Search
CPC ......... B01L 7/52; B01F 13/08; B01J 19/0013; G01N 33/442; A61F 2210/0004; A61L 27/58
USPC .......................................................... 436/2
See application file for complete search history.

(56) References Cited

U.S. PATENT DOCUMENTS

| 3,088,861 | A | 5/1963 | Mckee |
| 4,450,284 | A | 5/1984 | Sathe |
| 5,702,951 | A | 12/1997 | Bridger |
| 8,574,311 | B2 | 11/2013 | Yang et al. |
| 9,422,396 | B2 | 8/2016 | Younes |
| 2004/0180091 | A1 | 9/2004 | Lin |
| 2006/0034889 | A1 | 2/2006 | Jo et al. |
| 2007/0149640 | A1 | 6/2007 | Andjelic et al. |
| 2008/0243101 | A1 | 10/2008 | Andjelic et al. |
| 2009/0118241 | A1 | 5/2009 | Andjelic et al. |
| 2013/0236499 | A1 | 9/2013 | Andjelic et al. |
| 2013/0330827 | A1* | 12/2013 | Jamiolkowski ...... G01N 33/442 436/34 |
| 2015/0011814 | A1* | 1/2015 | Bhandarkar ............. C08F 2/01 585/503 |
| 2016/0008815 | A1 | 1/2016 | Porter et al. |

(Continued)

OTHER PUBLICATIONS

Kriksunov, L.B. et al. Development of Glass pH Sensors for use at Temperatures of 200-250C. Elsevier, Sensors and Actuators B: Chemical, vol. 22, issue 3, (Dec. 1994), pp. 201-204.

(Continued)

*Primary Examiner* — Matthew D Krcha
*Assistant Examiner* — Jacqueline Brazin
(74) *Attorney, Agent, or Firm* — David R. Crichton (57) ABSTRACT

A novel in vitro system and method for predicting the in vivo behavior, such as absorption time or mechanical strength retention, of biodegradable polymeric implants and medical devices. Data from this in vitro method are correlated to in vivo absorption data, allowing for the prediction of accurate in vivo behaviors, such as absorption times. The system uses a novel bypass loop to maintain the integrity of pH measuring devices to improve the reproducibility of data collected during in vitro testing.

12 Claims, 6 Drawing Sheets

(56) References Cited

U.S. PATENT DOCUMENTS

2017/0152328 A1* 6/2017 Odi ................... B01J 19/0013
2019/0381508 A1 12/2019 Han

OTHER PUBLICATIONS

Kriksunov, L.B. et al. "Tungsten/Tungsten Oxide pH Sensing Electrode for High Temperature Aqueous Environments". J Electrochem. Soc., vol. 141, No. 11, (Nov. 1994).
Bezwada, R.S. et al. "Monocryl®suture, a new ultra-pliable absorbable monofilament suture". Elsevier, Biomaterials, 16, (1995), pp. 1141-1148.
Craig, P.H. et al. "A Biological Comparison of Polyglactin 910 and Polyglycolic Acid Synthetic Absorbable Sutures". Elsevier, Surgery, Gynecology & Obstetrics, vol. 141, issue 1, (Jul. 1975) pp. 1-10.
International Search Report dated Jun. 10, 2020 for International Application No. PCT/IB19/54871.

* cited by examiner

ACCELERATED HYDROLYSIS SYSTEM

FIELD OF THE INVENTION

The field of art to which this invention relates is systems and methods for predicting the in vivo absorption time of bioabsorbable polymeric implants and medical devices, more specifically, in vitro systems and test methods for reliably predicting in vivo absorption times of bioabsorbable polymeric implants and medical devices in humans and mammals.

BACKGROUND OF THE INVENTION

Bioabsorbable polymers are known to have great utility in the medical field. They are particularly useful as surgical implants and medical devices. The bioabsorbable polymeric materials are designed to provide adequate strength and retention of mechanical properties in vivo to accomplish the function of the implant or medical device during the healing process, while degrading at a controlled and desired rate so that the device is essentially eliminated from the patient's body after natural healing has occurred and the implant or device is no longer required. Surgical implants and medical devices made from bioabsorbable polymers often provide superior patient outcome for many conditions and morbidities.

Synthetic absorbable polymers are an important class of materials used in a variety of implantable medical devices. Many of these devices, such as surgical sutures and surgical meshes, are used for soft tissue wound closure and repair applications. There are also orthopedic applications of such polymers for hard tissue (e.g., bone), including fixation devices such as pins, screws, plates, suture anchors, and longer lasting suture materials.

It is important to be able to predict the in vivo absorption times of implanted biodegradable polymeric medical devices for a number of reasons. There must be a degree of correlation between the length of time that the implants can retain their strength and mechanical properties in vivo and the length of time required for the healing process to progress to the point that the tissue can resume its normal functioning (i.e., breaking strength retention, "BSR"). Premature absorption and loss of mechanical strength and other mechanical properties may lead to a catastrophic failure resulting in injury to the patient, a failure of a surgical repair, or a life-threatening event requiring immediate medical intervention. In addition, it is beneficial to design the implant or device to have the minimum mass necessary to function adequately during the healing process.

As new absorbable polymers are being developed for medical devices and implants, a key issue is the length of time it will take for the material to disappear in the body, i.e., to absorb. This issue is also presented when designing new medical devices from conventionally known bioabsorbable polymers. Related to this issue is the desire to engineer medical devices and implants from bioabsorbable polymers that have desired absorption profiles in vivo. The definitive answer to this question is usually provided by preclinical studies using radiolabeled materials following the absorption, distribution, metabolism, and excretion of these materials and degradation products. The hydrolysis by-products may be converted to $CO_2$ exhaled or may be excreted in urine or feces. Radio-labeled materials can also be used to determine the fate or disposition of the materials, i.e., to determine whether the by-products are actually excreted or sequestered in target organs. Other important means for studying bioabsorption include histology in which a measurement of the cross-sectional area of the implant is made as a function of time. Of course, histology also provides important information on the tissue reaction that the implant elicits.

Traditional in vivo methods of assessing bioabsorption rates are expensive, time consuming, and obviously require the use of laboratory animals. Preclinical testing may be adequate to obtain regulatory approval and demonstrate safety and efficacy; however, there may be instances where human clinical trials may be required. In the case of the radiolabeled studies, typically an appropriately labeled $C_{14}$ monomer must be synthesized and scrupulously purified. The monomer must then be safely polymerized, and the resulting radioactive polymer must be converted to a test article possessing appropriate mechanical properties. In the case of a suture, this will typically require a strong, properly oriented fiber.

Broadly, from a humanitarian aspect, in vitro testing is preferred over animal testing, provided that useful, valid data is generated that can be correlated with in vivo performance having a high degree of statistically significant confidence. Additionally, although in vitro testing data can be collected under simulated physiological conditions, it is also desirable to collect such data in an accelerated fashion. Testing can be accelerated in some cases by changing temperature, pH, other parameters, or combinations thereof to obtain data in a quicker fashion than real-time testing. Product development cycle time can potentially be shortened by getting an early indication of performance, whether the focus is on the polymer composition or processing conditions used to make the article.

Clearly, it is advantageous to be able to estimate the rate of breakdown of a new bioabsorbable material, whether it is a different chemistry or an altered polymer morphology, without having to resort to radio-labeled or histological studies. This is also true for a new medical device made from known bioabsorbable materials. It is known that the biodegradation of bioabsorbable polyesters used in absorbable medical devices occurs via hydrolysis of ester linkages, with the by-product being acid generation. Generation of acid groups may not be troublesome to the surrounding tissue if the body's biological mechanisms can appropriately neutralize them as they are created. However, if a material undergoes too rapid hydrolysis, the tissues at the implant site may not be able to maintain a proper pH, thus causing undue inflammation.

Although conventional in vitro test methods are used to predict in vivo bioabsorption behavior, there may be deficiencies associated with their use. With some present methods, the data cannot be collected in an accelerated fashion. This is particularly troublesome for polymers having long absorption times. An example of this class of materials are those based on polymerized lactide; corresponding devices are often used in the field of orthopedics. Having a means of obtaining estimates of absorption time in an accelerated manner speeds development time and helps in product optimization. Clearly in vitro testing is advantageous over in vivo testing from a humane aspect in that animal use is significantly reduced or even eliminated. The costs associated with in vivo testing are significantly higher than the costs associated with in vitro testing. Although existing in vitro testing methods are adequate for their intended use, there is a need in this art for improved methods and systems to conduct in vitro testing. For example, it is required that conventional in vitro test systems maintain the solution baths at elevated temperatures substantially equal to or greater than body temperature. The elevated temperatures may adversely affect the performance of pH probes that are part of the in vitro titration systems, potentially resulting in incorrect data and resulting in miscalculated in vitro absorption times and incorrect predicted in vivo absorption times.

Accordingly, there is a need in this art for novel systems and methods for in vitro testing of bioabsorbable implants and medical devices that quickly, humanely, economically, accurately, and reproducibly predict in vivo bioabsorption times.

SUMMARY OF THE INVENTION

A novel system for performing in vitro testing of biodegradable specimens of bioabsorbable medical devices and bioabsorbable polymers is disclosed. The system has a mixing reactor bath vessel for containing a bioabsorbable specimen and an aqueous bath, the bath vessel having an inlet and an outlet and a mixer. A thermocouple is inserted into the bath vessel for measuring the temperature of the bath. A burette is inserted into the bath vessel for delivering a flow of a titrating base solution. There is a circulation pump having an inlet and an outlet and a pipe conduit for connecting the bath vessel outlet to an inlet of the circulation pump. The system has a cooler for cooling a bath stream having an inlet and an outlet and a pipe conduit for connecting the outlet of the pump to the inlet of the cooler. The system has a pH probe and a measuring vessel for holding the pH probe, the vessel having an inlet and an outlet and a pipe conduit for connecting the outlet of the cooler to the inlet of the measuring vessel. A pipe conduit connects the outlet of the measuring vessel to the inlet of the reactor bath vessel. There is a heat source associated with the bath vessel and there is a computer associated with the system to monitor, control and record the temperature and pH of the bath, the temperature of the bath stream out from the cooler, and the flow of base titrating solution to the bath, as a function of time.

Another aspect of the present invention is a novel system for performing in vitro testing of biodegradable specimens of bioabsorbable medical devices and bioabsorbable polymers. The system has a mixing reactor bath vessel for containing a bioabsorbable specimen and an aqueous bath, the bath vessel having an inlet and an outlet and a mixer. There is a thermocouple inserted into the bath vessel for measuring the temperature of the bath and a circulation pump having an inlet and an outlet. A pipe conduit connects the bath vessel outlet to an inlet of the circulation pump. The system has a bath stream cooler for cooling a bath stream having an inlet and an outlet and a pipe conduit for connecting the outlet of the pump to the inlet of the cooler. There is a cell vessel having an inlet and an outlet and a burette inserted into the cell vessel for delivering a flow of titrating base solution and a pipe conduit for connecting the outlet of the cooler to the inlet of the cell vessel. The system has a pH probe and a pH measuring vessel for holding the pH probe, the vessel having an inlet and an outlet, and a mixer. A pipe conduit connects the outlet of the cell vessel to the inlet of the pH measuring vessel. There is a bath stream heater for heating the bath stream having an inlet and an outlet and a pipe conduit for connecting the outlet of the pH measuring vessel to the inlet of the heater. A pipe conduit connects the outlet of the stream heater to the inlet of the reactor bath vessel. The system has a heat source associated with the bath vessel and, a computer associated with the system to monitor and record the temperature and pH of the bath, and the flow of titrating base solution to the bath, and the outlet temperatures of the bath streams exiting the bath stream cooler and the bath stream heater, as a function of time.

Yet another aspect of the present invention is a novel system for performing in vitro testing of biodegradable specimens of bioabsorbable medical devices and bioabsorbable polymers. The system has a heated mixing reactor bath vessel for containing a bioabsorbable specimen and an aqueous bath, the bath vessel having an inlet and an outlet and a mixer. A thermocouple is associated with the bath vessel for measuring the temperature of the bath. A burette is associated with the bath vessel for delivering a flow of a titrating base solution. The system has a pH probe and a measuring vessel for holding the pH probe, the measuring vessel having an inlet and an outlet in fluid communication with the reactor bath vessel for receiving and discharging a bath flow from the bath. There is a cooler for cooling the bath flow to the measuring vessel. And, there is a computer associated with the system to monitor, control, and record the temperature and pH of the bath and the flow of titrating base solution to the bath, and the temperature of the flow out from the cooler, as a function of time.

Still yet additional aspects of the present invention are methods of conducting in vitro testing of bioabsorbable polymers and test specimens utilizing the above-described systems.

These and other aspects and advantages of the present invention will become more apparent from the following description and accompanying drawings.

DETAILED DESCRIPTION OF THE INVENTION

It should be noted that the terms absorbable and bioabsorbable when referring to synthetic polymers are used interchangeably herein. A conventional hydrolysis profile method records as a function of time the amount of base needed to maintain the aqueous media at a selected constant pH while ester hydrolysis takes place. In doing so, it can be used to determine the time for achieving a relative fraction of hydrolysis, including complete hydrolysis. Those skilled in the art will recognize that many conventional equipment components may be used in the novel systems and methods of the present invention. Equipment may include for example a pH probe, glass vessels with temperature control, automatic dosing systems, data recording and remote instrument control capability, computers, processors, etc., and equivalents thereof. Control, data collection and analysis and presentation may be via conventional and/or customized computers and conventional and/or customized software and equivalents thereof.

Conventional in vitro testing methods consist of hydrolytically degrading a test specimen in a bath while maintaining a constant pH. This is done by titrating with a standard base (such as NaOH) and measuring the quantity of base used as a function of time. The measurement and titration are typically automated.

As part of the novel method of the present invention, in vitro work is conducted to completely hydrolyze an absorbable polyester surgical implant device, such as sutures at constant pH and elevated temperature. It should also be recognized that complete hydrolysis is not always needed, but hydrolysis levels greater than about 90% are preferred. This may be accomplished using the novel titrating systems of the present invention as further described herein. An absorbable polyester surgical suture (or other absorbable test article) is added to a reactor or reaction vessel containing, initially, only distilled water. The data can be recorded manually or with computer aid. In a preferred embodiment, the setup includes an electronic controller that takes the signal from the pH meter and causes a Teflon®-lined valve in the Teflon® tubing line to be opened in order to titrate the reaction so as to remain at a constant pre-determined pH set-point. Acid groups are generated as hydrolysis of the absorbable polyester suture (or bioabsorbable polymer test article) occurs, incrementally lowering the pH, as detected by the pH probe. The controller would then open the Teflon®-lined, electronically controlled valve, introducing base to titrate the mixture returning it to the pH set-point. The container of the dilute sodium hydroxide solution is mounted on an electronic balance, for example, so as to allow monitoring of the loss in weight as the NaOH solution is consumed during the hydrolysis process. Thus, through observation and manual recording, one can follow the extent of hydrolysis with time. With the use of computer control this basic methodology has been enhanced for convenience, accuracy, and standardization. It will be appreciated by those skilled in the art that the procedure can be performed manually without automatic controllers if desired, although not preferred.

The systems and methodologies of the present invention may be applied to polymers possessing esters in their backbones. The methods may also be applicable, in modified form, to gain insight into the degradation of candidate polymer systems, for instance those containing esters in pendant groups. The pendant ester hydrolysis may lead to chain segment solubilization or in other instances, depending on the chemistry, lead to main chain degradation because of local pH changes, a so called "neighboring group effect".

The hydrolysis profiler method presented here applies to conventional synthetic absorbable polyesters, polyanhydrides, and other polymers with hydrolytically degradable linkages, and equivalents thereof that yield acidic degradation products.

The bioabsorbable polymers that can be used to make devices that can be tested according to the method of the present invention include conventional biocompatible, bioabsorbable polymers including polymers selected from the group consisting of aliphatic polyesters, poly(amino acids), copoly(ether-esters), polyalkylene oxalates, polyalkylene diglycolates, polyamides, tyrosine-derived polycarbonates, poly(iminocarbonates), polyorthoesters, polyoxaesters, polyamidoesters, polyoxaesters containing amine groups, poly(anhydrides), polyphosphazenes, poly(propylene fumarates), absorbable poly(ester urethanes), and combinations and blends thereof, and equivalents. The polyoxaesters include the polymers based on 3,6-dioxaoctanedioic acid, 3,6,9-trioxaundecanedioic acid, and the diacid known as polyglycol diacid, which can be made from the oxidation of low molecular weight polyethylene glycol.

Suitable polymers can be homopolymers or copolymers (random, block, segmented, tapered blocks, graft, triblock, etc.) having a linear, branched or star structure. Suitable monomers for making suitable polymers may comprise one or more of the following monomers: lactic acid (including L-lactic acid and D-lactic acid), lactide (including L-, D-, meso and D,L-mixtures), glycolic acid, glycolide, ε-caprolactone, p-dioxanone (1,4-dioxan-2-one), trimethylene carbonate (1,3-dioxan-2-one), δ-valerolactone, ε-decalactone, 2,5-diketomorpholine (morpholinedione), pivalactone, α,α-diethylpropiolactone, ethylene carbonate, ethylene oxalate, 3-methyl-1,4-dioxane-2,5-dione, 3,3-diethyl-1,4,dioxan-2,5-dione, γ-butyrolactone, 1,4-dioxepan-2-one, 1,5-dioxepan-2-one, 6,6-dimethyl-dioxepan-2-one, 6,8-dioxabicycloctane-7-one or combinations thereof. It is to be understood that the methods of the present invention can be applied to polymer blends.

Alternately the bioabsorbable polymers can be a component of a cross-linked network. That is, suitable polymers also include cross-linked polymers and hydrogels possessing hydrolysable ester or anhydride groups. It is to be understood that exemplary bioabsorbable, biocompatible polymers may be generally synthesized by a ring-opening polymerization of the corresponding lactone monomers or by polycondensation of the corresponding hydroxy-acids, or by combinations of these two polymerization methodologies.

As new absorbable polymers are being developed for medical devices and implants, a key issue is the length of time it will take for the material to disappear in the body, i.e., to absorb. Related to this issue is the desire to engineer medical devices and implants from bioabsorbable polymers that have desired absorption profiles in vivo. Although the definitive answer to this question is usually provided by preclinical studies using radiolabeled materials following the absorption, distribution, metabolism, and excretion of these materials and degradation products, other important means for studying bioabsorption include histology in which a measurement of the cross-sectional area of the implant is made as a function of time. For instance, the paper entitled "Monocryl® Suture, a New Ultra-Pliable Absorbable Monofilament Suture", by Rao S. Bezwada, Dennis D. Jamiolkowski, In-Young Lee, Vishvaroop Agarwal, Joseph Persivale, Susan Trenka-Benthin, Modesto Erneta, Jogendra Suryadevara, Alan Yang, and Sylvia Liu appearing in Biomaterials, Volume 16, Issue 15, October 1995, Pages 1141-1148 describes the biological performance of a monofilament suture based on caprolactone and glycolide. Another example of such studies is the work of Craig, P. H., Williams, J. A., Davis, K. W., Magoun, A. D., Levy, A. J., Bogdansky, S., and Jones, J. P. Jr. as reported in a paper entitled "A Biologic Comparison of Polyglactin 910 and Polyglycolic Acid Synthetic Absorbable Sutures" in Surg. Gynecol. Obstet., 141:1-10, 1975. Both of these papers are incorporated by reference.

Typically, in vivo performance of absorbable medical devices is commonly obtained in preclinical rat models. As described above, for sutures in vivo performance in Long-Evans rats has been used, where sutures are implanted in gluteal muscles and harvested at selected time points post-implantation where they are sectioned and stained for histological evaluation. In vivo absorption is thus typically evaluated in these models via tracking the disappearance of the implant in histologically prepared tissue sections.

The mechanical performance of absorbable medical devices changes with time in an in vivo environment. The failure mode of these devices may be dependent on one or more mechanical characteristics, for example, elongation-to-break, Young's Modulus, tensile strength, recovery characteristics, or tear strength. Since the mechanical performance is a function of the molecular weight and the molecular weight in turn depends on the extent of hydrolysis one might use the method of the present invention to predict mechanical property performance.

Although the hydrolysis profiler runs presented in the included examples hereinbelow were generally done at 70° C., other sufficiently effective temperature and pH conditions and other parameters can be utilized and explored, and correlations to in vivo behavior (such as absorption times or loss of mechanical properties) sought. A broad family of correlations may be possible provided that there are no major changes in the basic mechanisms of degradation. The temperature range may typically be greater than about 37° C., more typically about 60° C. to about 95° C., preferably about 70° C. to about 75° C., and most preferably about 70° C. The pH may range from typically greater than about 2 to about 11, more typically about 6.3 to about 8.3, and preferably about 7.3. The concentration of aqueous sodium hydroxide titrating base solution will typically be about 0.0001N to about 1.0N, more typically about 0.05N. The constant level of percent hydrolysis of the test article will typically be about 90% to about 100%, more typically about 95% to about 100%, preferably about 98% to about 100%, and even more preferably about 100%.

It is expected that changes in physical properties of a given material (such as suture breaking strength retention) are related to its hydrolysis profile as chemical degradation influences mechanical performance.

Since load bearing in semi-crystalline polymers is dependent on so-called "tie molecules" present in the amorphous phase but connecting crystallites, cleavage of these molecules, and not the chain segments in crystallites, controls strength retention. It is then expected that the amount of hydrolysis needed to occur to influence tensile strength in semi-crystalline polymers will be very small; within the first few percent after the hydrolysis of any residual monomer. To access this information experimentally, one may need to use a more dilute titrant, and/or a lower test temperature, and possibly increase the rate of data collection in the early part of the hydrolysis profile. A new set of correlation curves would need to be generated to relate the early portion of the hydrolysis profile to in vivo mechanical performance.

It is to be understood that high test temperatures might be limited by the boiling point of water. In cases where high acceleration is sought, a sealed system might be employed in which pressures greater than one atmosphere might be used.

It is also to be understood that relatively low test temperatures, provided that they are above body temperature, may be used. This may be particularly useful in the case of low-melting polymers. It is further understood that provided an activation energy of hydrolysis is known, data can be collected at a given test temperature and predictions of in vivo hydrolysis made using correlation curves based on in vitro data collected at a different temperature.

Regarding the role of sample size, it is to be understood that a sample size sufficiently large to effectively minimize experimental variation is required. When the sample size is too low variability in results will occur. It should be noted that very large sample sizes may then require very large hydrolysis reactors.

It is to be understood that a given correlation curve must be built using the same test conditions as is used for the test article being assessed.

Regarding the initial amount of water in the hydrolysis vessel, it is to be understood that a sufficient volume of water to effectively cover the test article in the hydrolysis vessel will be required. The hydrolysis vessel should have adequate spare volume to accommodate the test article, initial quantity of water and the final volume of titrating base solution.

It is to be understood that one could additionally include a color-changing pH indicator and a means of monitoring the color in order to control the titration to maintain the substantially constant test pH.

It should also be understood that in cases where enzymatic degradation pathways are significant, the in vitro to in vivo correlation may not hold. In these cases, one may need to add appropriate enzymes in suitable amounts to the reaction media.

A representative listing of bioabsorbable medical devices and implants that can be tested by the apparatus and methods of the present invention includes but is not limited to, test coupons, sutures, tacks, meshes, staples, bone pins, bone plates, screws, ligating clips, staples, knot clips, etc.

To construct an in vivo—in vitro correlation curve (for instance of in vivo absorption time versus in vitro hydrolysis time) one might employ a variety of methods. It is useful to obtain a mathematical equation describing the relationship, whether it is linear or non-linear. If the response curve is linear, a well-accepted methodology of obtaining the mathematical descriptive equation is by performing a linear regression using the Method of Least Squares.

The novel in vitro systems and methods or methodology of the present invention, which are used to predict the in vivo absorption time of bioabsorbable polymeric implants and medical devices, have many advantages. The advantages include the following. It has been demonstrated that absorbable polyesters can be characterized for extent of hydrolytic degradation as a function of time under accelerated conditions. This includes above body temperature, and does not exclude temperatures above the glass transition temperature of the polymeric test article. Other means of acceleration of hydrolysis whereby degradation could occur at body temperature will be evident to one having ordinary skill, these include lower or higher pH than in the examples presented. Alternate means of acceleration may be useful when characterizing devices that may not be dimensionally stable (e.g., shrinking or melting) at elevated temperatures. Additionally, the systems and methods of the present invention have been found to provide more reliable hydrolysis data and more reliable hydrolysis profiles.

One of the utilities of the hydrolysis profiler technology is that it may reduce the need for animal testing. For example, to design in vivo tissue reaction and absorption studies on a new medical device based on a new absorbable polymer, it is necessary to conduct preclinical animal studies. For a new material, the end-point times for the preclinical studies are unknown, and additional animal groups are needed to ensure histology samples are collected during all significant material changes. The hydrolysis profiler may allow for the elimination of some of the extra animal groups, since the times of significant material change can be reasonably predicted.

Thus, if one can reasonably predict that an absorbable polymeric medical device will absorb at approximately 180 days post-implantation, one could focus on animal test periods centered in this time frame, rather than a larger number of more randomly selected test periods, which may not yield useful results. This then assists in establishing an effective animal testing plan.

Figure 1:
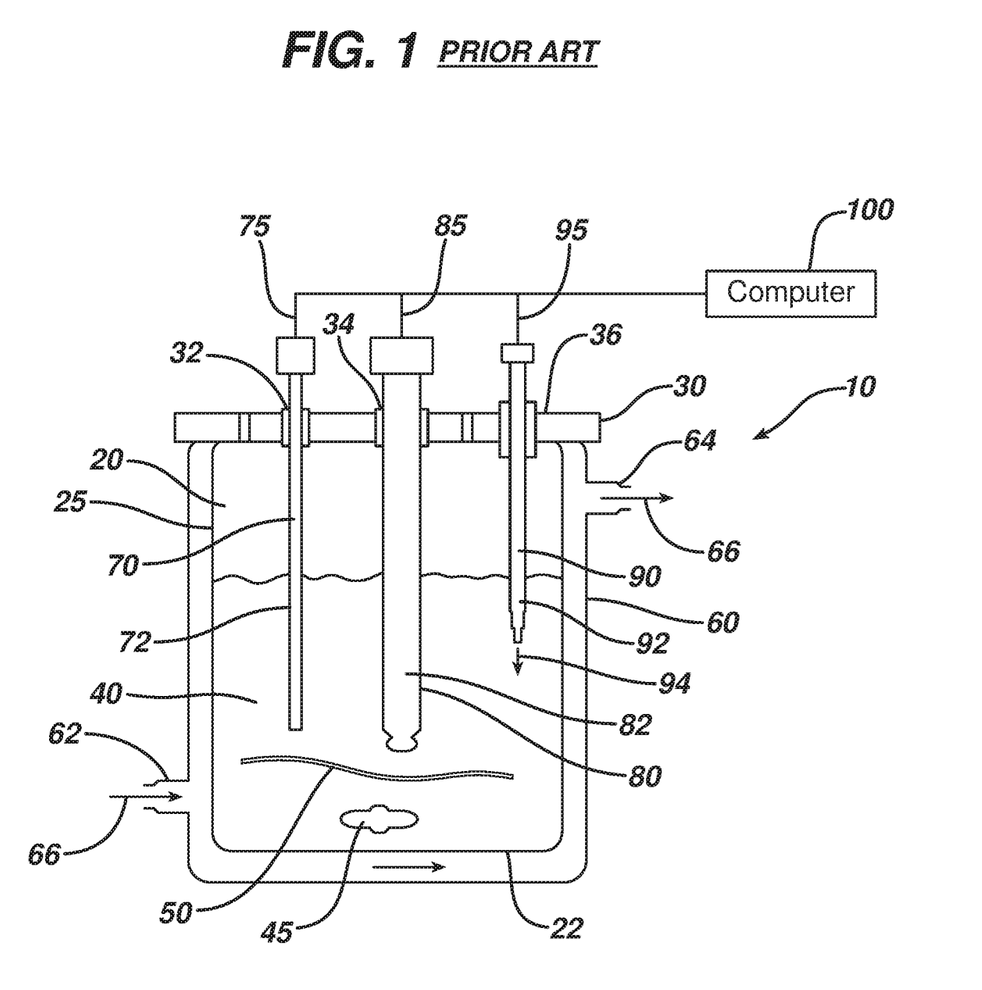
FIG. 1 is a schematic diagram of a hydrolysis system of the prior art showing the pH probe, thermocouple, and burette in a heated bath contained in the reaction vessel.

The in vitro testing systems of the present invention are described as follows. Referring initially to FIG. 1, a hydrolysis system 10 of the prior art is illustrated. The system 10 is seen to have a reaction vessel 20. Reactor vessel 20 is a generally cylindrically shaped vessel having sidewall 25, bottom 22 and sealed top 30. Top 30 is sealed to prevent evaporation of the bath 40. Contained in the vessel 20 is the bath 40. Bath 40 will consist of a typical, suitable fluid such as deionized water. Stirrer 45 is seen to be located in bath 40 adjacent to bottom 22 of vessel 20. Sample 50 comprising a bioabsorbable polymer is suspended in bath 40. Surrounding vessel 20 is a conventional heating jacket 60, preferably an oil bath, having lower inlet 62 and upper outlet 64. The conventional oil heating media 66 is heated by a conventional heater (not shown) connected between the outlet 64 and the inlet 62. Inserted into vessel 20 through opening 32 in top 30 is the thermocouple 70. The thermocouple body 72 is at least partially submerged in bath 40. The pH probe 80 is seen to me inserted into vessel 20 through opening 34. The pH probe 80 having pH probe body 82 is at least partially submerged in bath 40. Also inserted into vessel 20 through opening 36 of top 30 is the burette 90 having burette body 92. The burette body 92 is at least partially submerged in bath 40. The system 10 operates in the following manner. Connected to thermocouple 70, pH probe 80 and burette 90 are the electrical conductors or leads 75, 85, and 95, respectively. The leads 75, 85 and 95 are connected to conventional computer controller 100. Computer controller monitors input from thermocouple 70 and pH probe 80, and attempts to maintain the bath 40 at a set temperature and set pH by controlling the flow and temperature of heating oil into heating jacket 60, and controlling and recording the flow of titrating solution 94 (e.g., 0.05N NaOH solution) into the bath 40 through the burette 90. The temperature and pH of bath 40, and the volume of titrating solution 94 flowing into bath 40 are recorded by the computer as a function of time.

Figure 3:
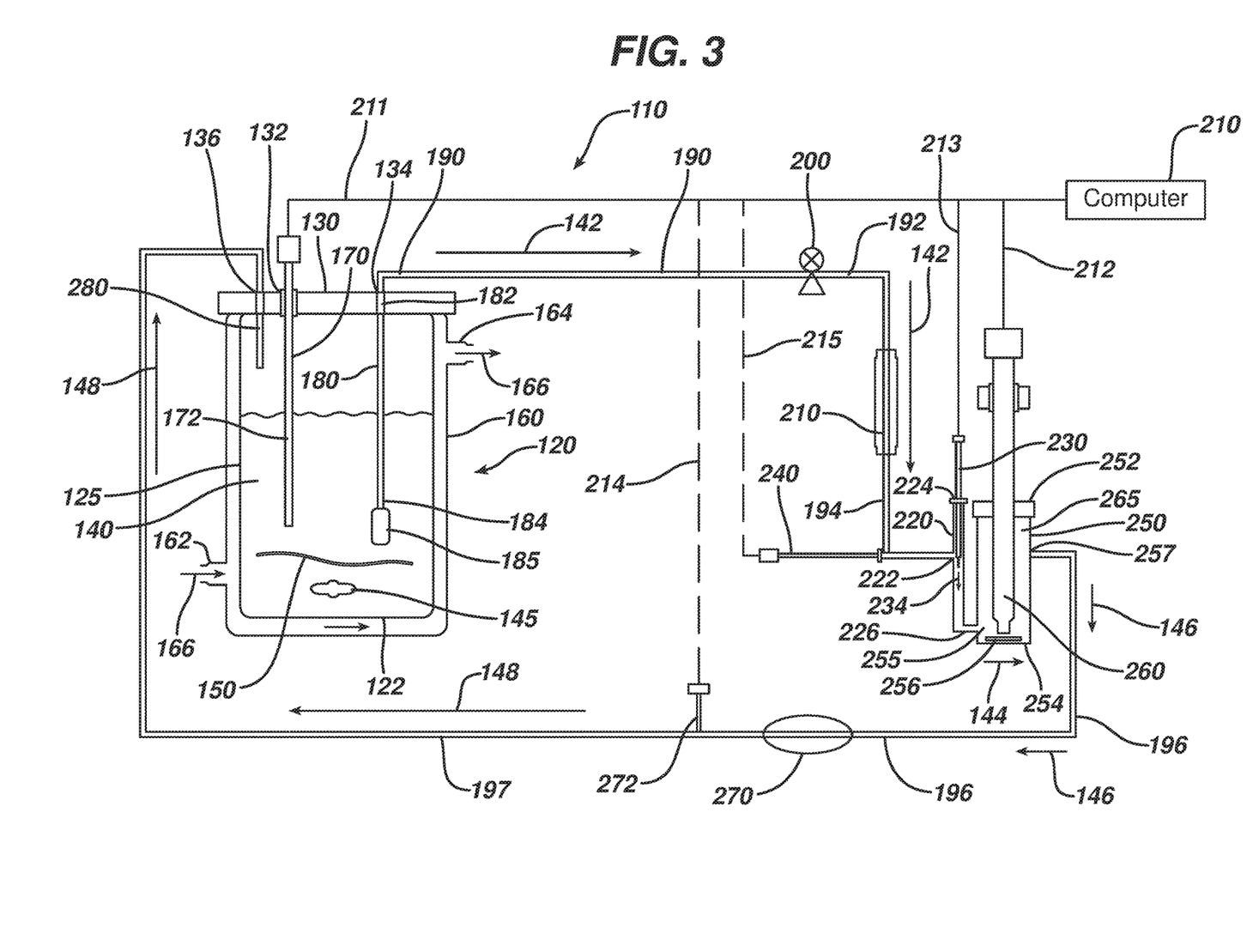
FIG. 3. is a diagram of an embodiment of a novel system of the present invention having the burette located in a pipe circuit outside of the reaction vessel and the pH probe located in a separate vessel connected to the circuit outside of the reaction vessel.

An embodiment of a novel hydrolysis system 110 of the present invention is seen in FIG. 3. System 110 is seen to have a reaction vessel 120. Reactor vessel 120 is a generally cylindrically shaped vessel having sidewall 125, bottom 122 and sealed top 130. Top 130 is sealed to prevent evaporation of the bath 140. Contained in the vessel 120 is the bath 140. Bath 140 will consist of a typical, suitable fluid such as deionized water. Stirring bar 145 is seen to be located in bath 140 adjacent to bottom 122 of vessel 120. Sample 150 comprising a bioabsorbable polymer is suspended in bath 140. Surrounding vessel 120 is a conventional heating jacket 160, preferably an oil bath, having lower inlet 162 and upper outlet 164. The conventional oil heating media 166 is heated by a conventional heater (not shown) connected between the outlet 164 and the inlet 162. Inserted through opening 132 in top 130 is the thermocouple 170. The thermocouple body 172 is at least partially submerged in bath 140. System 110 is seen to have outflow pipe 180 extending into vessel 120 through opening 134 in top 130. The outflow pipe is seen to have top 182 and bottom 184. Bottom 184 is submerged in bath 140 and is connected to filter 185. The top 182 of outlet pipe 180 is connected to pipe member 190. Bath outlet flow stream 142 is contained in pipe member 190. Pipe member 190 is connected downstream to the inlet of pump 200. The outlet of pump 200 is connected to pipe member 192 which is connected to the inlet of cooling device 210; pipe member 192 directs flow stream 142 to cooling device 210. The outlet of cooling device 210 is connected to pipe member 194 which directs the cooled bath outlet flow stream 142 to the side inlet 222 of burette receiving cell 220. Burette receiving cell 220 is seen to be a tube-like member having top 224 and bottom outlet 226. Burette 230 is seen to be inserted through top 224 into the interior of burette receiving cell 220. Titrating solution 234 (e.g., 0.05N NaOH solution) flows from burette 230 into receiving cell 220. Thermocouple 240 is seen to be emplaced in pipe member 194 between the discharge of cooling device 210 and the side inlet 222 such that it can measure the temperature of outlet stream 142 at that location. The bottom side outlet 226 of burette receiving tube 220 is seen to be connected to pH measuring vessel 250. The pH measuring vessel 250 is a cylindrical vessel having a top 252 and a bottom 254 and stirring bar 256. Vessel 250 has bottom side inlet 255 connected to bottom side outlet 226 for receiving flow stream 144. The pH probe 260 is seen to be inserted at least partially into the pH measuring vessel 250 through top 252 into pH adjusted bath 265. The exit flow stream 146 is seen to exit the upper side discharge outlet 257 which is connected to pipe member 196. Pipe member 196 is seen to connect to the inlet side of heater 270. The outlet side of heater 270 is connected to pipe member 197 which directs the inlet stream flow stream 148 to the inlet tube 280 of reactor vessel 120 and into bath 140 containing sample 150. Inlet tube 280 is seen to be inserted through top 130 at opening 136. A thermocouple 272 is emplaced in pipe member 197 adjacent to the discharge of heater 270 to measure the temperature of stream 148. Computer 210 monitors and controls the system via data inputs and outputs through the leads 211, 212, and 213, 214 and 215. The various temperatures, pH and volume of titrating solution are recorded as a function of time.

Figure 5:
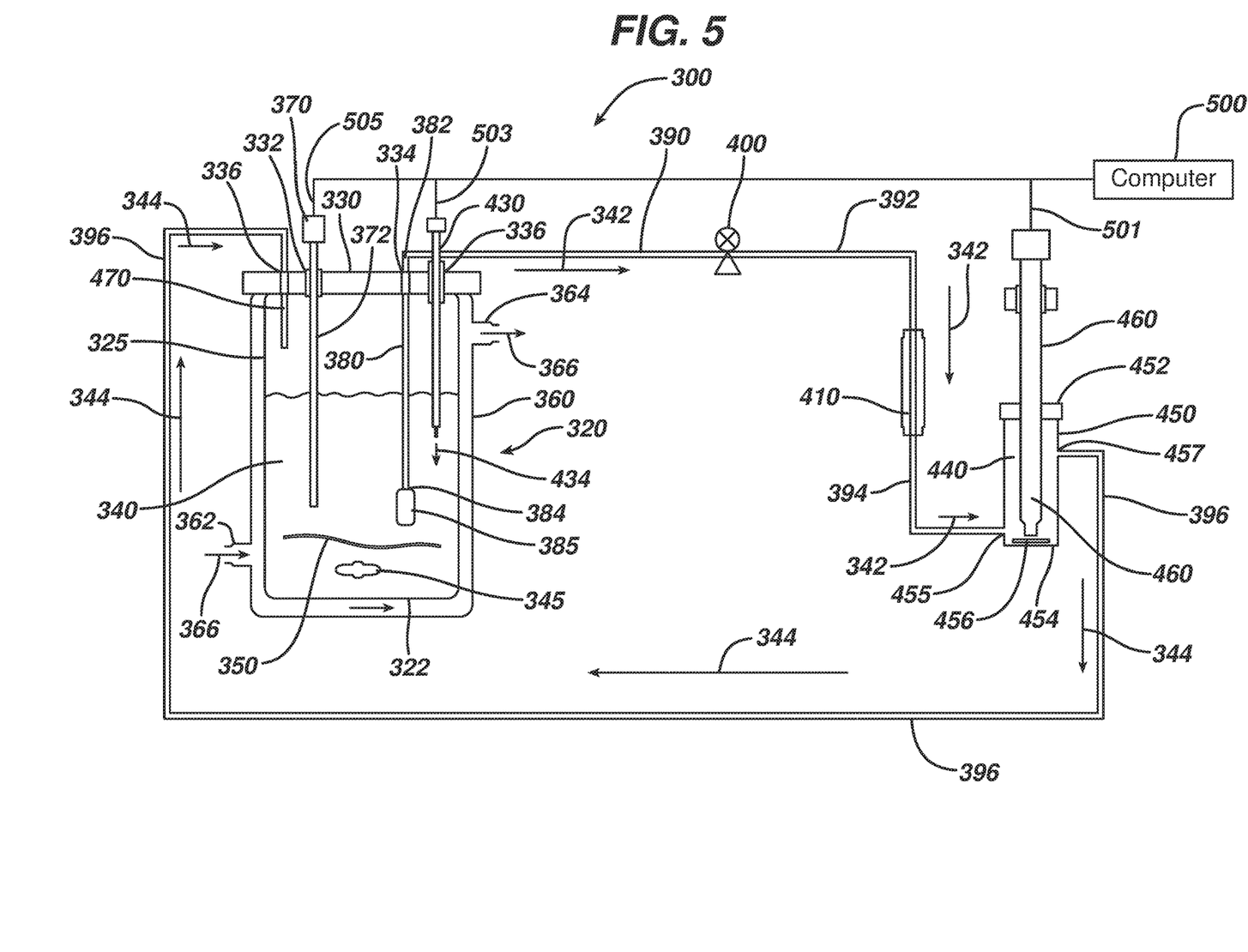
FIG. 5 is a diagram of an alternate embodiment of a novel system of the present invention with the burette located in the reaction vessel and the pH probe located in a separate vessel connected to a pipe circuit outside of the reaction vessel.

In operation, the systems 110 and 300 (described below) provide data for in vitro degradation times that can be used to predict in vivo degradation and breaking strength retention. System 110 operates in the following manner. Initially, a sufficiently effective volume of deionized water is placed into reaction vessel 120 to form bath 140. The temperature of bath 140 is raised to a sufficiently effective temperature to conduct the in vitro testing. The temperature of the bath is maintained at the desired temperature by the heating jacket 160 which is controlled by a feedback loop based upon readings from thermocouple 170. The temperature of bath 140 will typically range from about 70° C. to about 95° C. Sample 150 (e.g., one or more 1" lengths of suture) is then inserted into bath 140 in a conventional manner, and top 130 is mounted to seal reactor vessel 120. The stirring bar 145 is engaged (by a conventional magnetic stirrer bar) either before or after immersion of the sample 150 in bath 140. Bath flow outlet stream 142 is then moved out from reaction vessel 120 through outflow pipe 180 through pipe 190 to the inlet of pump 200. The pump 200 directs flow stream 142 to the inlet of cooling device 210 through pipe member 192. Cooling device 210 cools flow stream 142 to a suitable temperature to effectively allow accurate pH measurements to be taken, e.g., 20° C. to about 40° C. The cooled flow stream 142 is directed to the side inlet 222 of burette receiving cell 220. The pH of flow stream 142 is adjusted in cell 220 by a flow of titrating solution 234 from burette 230. The pH adjusted flow stream 144 exits the bottom outlet of cell 220 and is directed to bottom side inlet 255 of pH measuring vessel 250. The pH probe 260 measures the pH of pH adjusted bath 265. Output from pH probe 260 is sent to computer 210, which utilizes the data to send a signal to burette 230 to send a sufficient amount of titrating solution 234 into cell 220 to change the pH of flow stream 144 to sufficiently effective value, for example about 7.15 to about 7.25. The flow stream 146 is then seen to move from outlet 257 through pipe member 196 to the inlet of heater 270. The heated flow stream 148 exits the outlet side of heater 270 and is directed through pipe member 197 which directs the inlet stream flow stream 148 to the inlet tube 280 of reactor vessel 120 and into bath 140 containing sample 150. The flow stream 148 is heated by heater 148 to a temperature approximately the same as the temperature of bath 140, for example about 70° C. to about 95° C. The temperatures of flow streams 142 and 148 are monitored by thermocouples 240 and 272, respectively, which send data outputs to computer 210 for controlling the flow stream temperatures from cooling device 210 and heating device 270. The various temperatures, pH and volume of titrating solution are recorded by computer 210 as a function of time.

An alternate embodiment of a novel system 300 of the present invention is illustrated diagrammatically in FIG. 5. System 300 is seen to have a reaction or reactor vessel 320. Reactor vessel 320 is a generally cylindrically shaped vessel having sidewall 325, bottom 322 and sealed top 330. Top 330 is sealed to prevent evaporation of the bath 340. Contained in the vessel 320 is the bath 340. Bath 340 will consist of a typical, suitable fluid such as deionized water. Stirrer or stirring bar 345 is seen to be located in bath 340 adjacent to bottom 322 of vessel 320. Sample 350 comprising a bioabsorbable polymer is suspended in bath 340. Surrounding vessel 320 is a conventional heating jacket 360, preferably an oil bath, having lower inlet 362 and upper outlet 364. The conventional oil heating media 366 is heated by a conventional heater (not shown) connected between the outlet 364 and the inlet 362. Inserted through opening 332 in top 330 is the thermocouple 370. The thermocouple body 372 is at least partially submerged in bath 340. Also inserted through opening 336 in top 330 is the burette 430. Titrating fluid 434 is discharged through burette 430 into bath 340. System 300 is seen to have outflow pipe 380 extending into vessel 320 through opening 334 in top 330. The outflow pipe is seen to have top 382 and bottom 384. Bottom 384 is submerged in bath 140 and is connected to filter 385. The top 382 of outlet pipe 380 is connected to pipe member 390. Bath outlet flow stream 342 is contained in pipe member 390. Pipe member 390 is connected downstream to the inlet of pump 400. The outlet of pump 400 is connected to pipe member 392 which is connected to the inlet of cooling device 410. The outlet of cooling device 410 is connected to pipe member 394 which directs the cooled bath outlet flow stream 342 to pH measuring vessel 450. Pipe member 394 is connected to the bottom side inlet 455 of vessel 450. The pH measuring vessel 450 is a cylindrical vessel having a top 452 and a bottom 454 and stirring bar 456. Vessel 450 has bottom side inlet 455 connected to pipe member 394 for receiving flow 342. The pH probe 460 is seen to be inserted at least partially into the pH measuring vessel 450 thorough top 452 into pH measuring bath 440. The outlet flow stream 344 is seen to exit the upper side discharge outlet 457 which is connected to pipe member 396. Pipe member 396 is seen to connect to the inlet tube 470 of reactor vessel 320 which directs flow stream 344 into bath 340 containing sample 350. Inlet tube 470 is seen to be inserted through top 330 at opening 336. Computer 500 monitors and controls the system via data inputs and outputs through the leads 501, 503 and 505. The various temperatures, pH and volume of titrating solution are recorded as a function of time.

System 300 operates in the following manner. Initially, a sufficiently effective volume of deionized water is placed into reaction vessel 320 to form bath 340. The temperature of bath 340 is raised to a sufficiently effective temperature to conduct the in vitro testing. The temperature of the bath 340 is maintained at the desired temperature by the heating jacket 360 which is controlled by a feedback loop based upon readings from thermocouple 370. The temperature of bath 340 will typically range from about 70° C. to about 95° C. Sample 350 is then inserted into bath 340 in a conventional manner, and top 330 is mounted to seal reactor vessel 320. The stirring bar 345 is engaged (by a conventional magnetic drive) either before or after immersion of the sample 350 in bath 340. Bath flow outlet stream 342 is then moved out from reaction vessel 320 through outflow pipe 380 through pipe 390 to the inlet of pump 400. The pump 400 directs flow stream 342 to the inlet of cooling device 410 through pipe member 392. Cooling device 410 cools flow stream 344 to a suitable temperature to effectively allow accurate pH measurements to be taken, e.g., the temperature may range from 20° C. to about 40° C. The cooled flow stream 342 is directed to the side inlet 455 of pH measuring vessel 450 containing bath 440. The flow stream 344 exits the top side outlet 457 and is directed through pipe member 396 to the inlet tube 470 of reactor vessel 320. The pH probe 460 measures the pH of bath 440. Output from pH probe 460 is sent to computer 500, which utilizes the data to send a signal to burette 430 to send a sufficient amount of titrating base solution 434 into bath 340 to change the pH of bath 340 to the desired pH, for example, to about 6 to about 9. The various temperatures, pH and volume of titrating solution are recorded and controlled by computer 210 as a function of time.

The following examples are illustrative of the principles and practice of the present invention although not limited thereto.

EXAMPLE 1

Hydrolysis Experiment with a Conventional System of the Prior Art (FIG. 1)

Four identical 718 STAT Titrinos made by Metrohm with Tiamo Software to control the pH of the reaction were used for this example, see FIG. 1. The reaction temperature was controlled by an oil bath circulator made by LAUDR (Type E203). Both the burette and pH probe were placed inside of the reaction vessel.

A sample of VICRYL® (polyglactin 910) Suture, Size 2/0 was used, available from Ethicon, Inc., Somerville, N.J. 08876.

Prior to sample run, the pH probe of the Titrino was calibrated with pH 4.0, 7.0, and 10.0 standard solutions. After pH probe calibration, 100 mL of deionized water was added in a conventional 100 mL double-jacketed glass reaction vessel. The vessel was magnetically stirred and heated to 70° C. About 100 mg±0.5 mg polymer samples were added. The vessel was fitted with a sealed lid to prevent evaporation, a pressure of one atmosphere was maintained and a pH setpoint of 7.25 was used to control the hydrolysis reaction.

The hydrolysis reaction was continuously monitored for pH changes (drops in pH) from the setpoint. If any decrease of pH was detected by Titrator, 0.05N sodium hydroxide solution was added into the reaction vessel to return the pH to the setpoint automatically by Titrator. The pH, temperature, and volume of 0.05N sodium hydroxide added to reaction vessel were recorded by a computer as a function of time. % degradation was calculated according to following formula and plotted against time:

% degradation=$V(t)/V(total)\times 100$

V(t)=NaOH volume used up to a timepoint; V(total)=total NaOH volume used.

Figure 2:
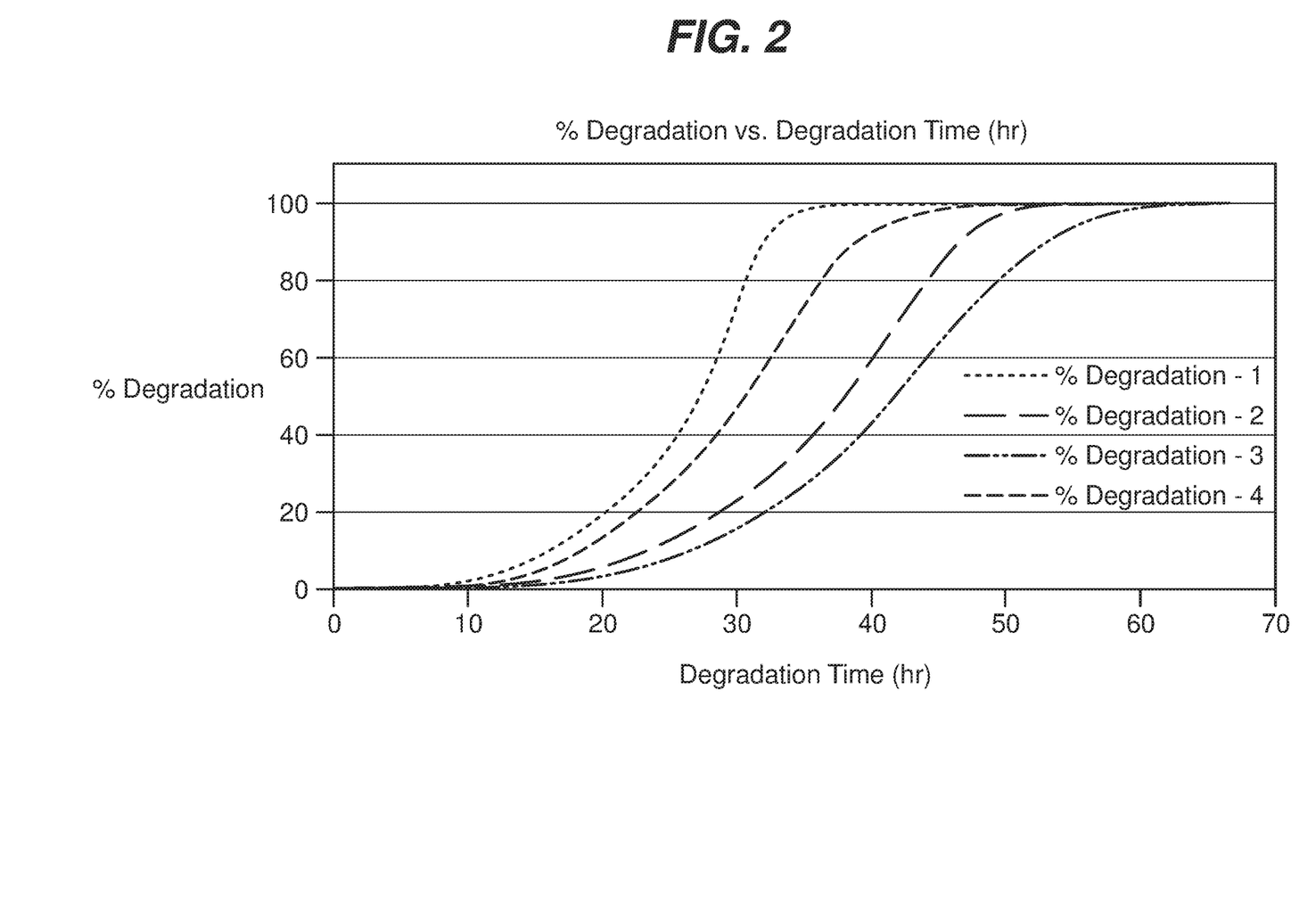
FIG. 2 is a graph showing four hydrolysis reactions (degradation-1, degradation-2, degradation-3, degradation-4) that were run on the same sample with four identical instrument setups at the same time using the prior art system of FIG. 1.

As seen in FIG. 2, the results showed that the hydrolysis profiles were not repeatable and data were not reliable; it is believed, simply that the pH probes were not designed for continuing measurement at high temperature for long duration.

EXAMPLE 2

Hydrolysis Experiment with a Modified System (FIG. 5) with Burette Placed Inside of Reaction Vessel and pH Probe Placed Outside of Reaction Vessel A 902 Titrando made by Metrohm with Tiamo Software to control the pH of the reaction was used for this example (see FIG. 5). The reaction temperature was controlled by an oil bath circulator made by LAUDR (Type E203). A custom-made pH probe cell was used to hold pH probe for measuring the pH, the pH probe was not placed in the reaction vessel. A FMI "Q" Pump made by CERAMPUMP (Model QG 50) was used to circulate hot reaction solution from the reaction vessel through the 20 μm filter into a custom-made coil cooled by Agilent column cooling device (model G1316A) to bring the hot solution to below 30° C. The circulation speed was set at about 8 ml/min. The burette was placed inside of reaction vessel.

A sample of VICRYL® (polyglactin 910) Suture, Size 2/0 was used, available from Ethicon, Inc., Somerville, N.J. 08876.

Prior to sample run, the pH probe of the Titrando was calibrated with pH 4.0, 7.0, and 10.0 standard solutions. After pH probe calibration, 100 mL of deionized water was added in a conventional 100 mL double-jacketed glass reaction vessel. The vessel was magnetically stirred and heated to 70° C. About 100 mg±0.5 mg polymer samples were added. The vessel was fitted with a sealed lid to prevent evaporation, a pressure of one atmosphere was maintained and a pH setpoint of 7.25 was used to control the hydrolysis reaction.

Figure 6:
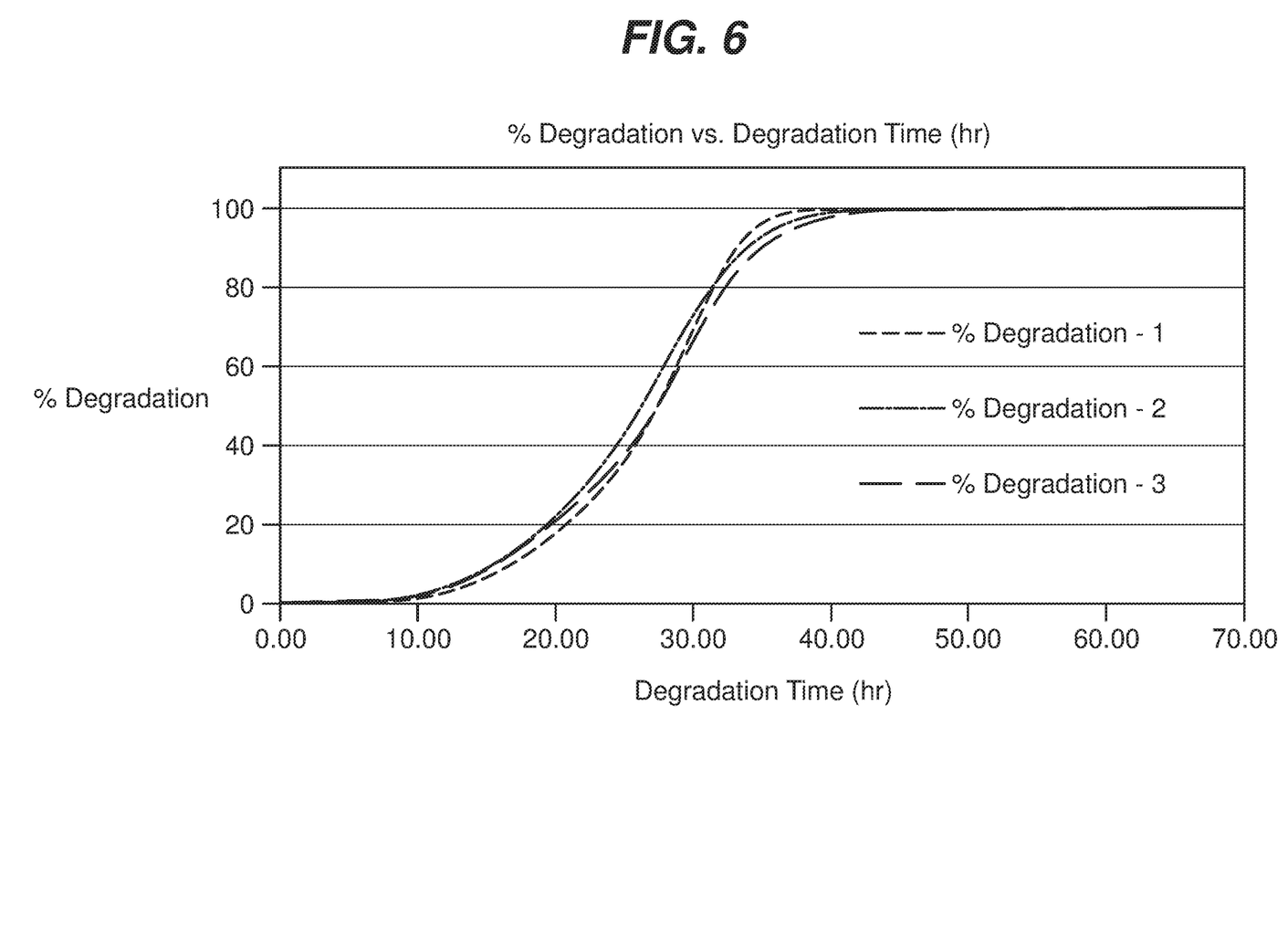
FIG. 6 is a graph showing three hydrolysis reactions (degradation-1, degradation-2, degradation-3) which were run on the same sample with the system of FIG. 5. The burette was placed inside of the reaction vessel and the pH probe was placed outside of the reaction vessel.

The hydrolysis reaction was continuously monitored in the pH probe cell for pH changes (drops in pH) from the setpoint. If any decrease of pH was detected by Titrando, 0.05N sodium hydroxide solution was added into the vessel to return the pH to the setpoint automatically. The pH, temperature, and volume of 0.05N sodium hydroxide added to hydrolysis vessel were recorded by computer as a function of time. % degradation was calculated and plotted against time (see FIG. 6) according to the following formula:

% degradation=$V(t)/V(total)\times 100$

V(t)=NaOH volume used up to a timepoint; V(total)=total NaOH volume used.

The results showed, by placing the pH probe outside of reaction vessel in a cell and maintaining a constant temperature of the bath flow in the cell, the hydrolysis profiles were significantly more repeatable and the data was significantly more reliable.

EXAMPLE 3

Hydrolysis Experiment with a Modified System (FIG. 3) with Both pH Probe and Burette Placed Outside of Reaction Vessel Two 902 Titrandos made by Metrohm with Tiamo Software to control the pH of the reaction were used for this example (see FIG. 3). The reaction temperature was controlled by an oil bath circulator made by LAUDR (Type E203). A custom-made pH probe cell was used to hold pH probe and burette for measuring and adjusting the pH. A FMI "Q" Pump made by CERAMPUMP (Model QG 50) placed before cooling device or Agilent HPLC pump (model G1311 QuatPump) placed after cooling device was used to circulate hot reaction solution from the reaction vessel through the 20 μm filter into a custom-made coil cooled by Agilent column cooling device (model G1316A) to bring the hot solution below to 30° C. The circulation speed was set at about 8 ml/min.

A sample of PDS II Suture, Size 2/0 was used, available from Ethicon, Inc., Somerville, N.J. 08876.

Prior to sample run, the pH probe of the Titrando was calibrated with pH 4.0, 7.0, and 10.0 standard solutions. After pH probe calibration, 100 mL of deionized water was added in a conventional 100 mL double-jacketed glass reaction vessel. The vessel was magnetically stirred and heated to 70° C. About 100 mg±0.5 mg polymer samples were added. The vessel was fitted with a sealed lid to prevent evaporation, a pressure of one atmosphere was maintained and a pH setpoint of 7.25 was used to control the hydrolysis reaction.

Figure 4:
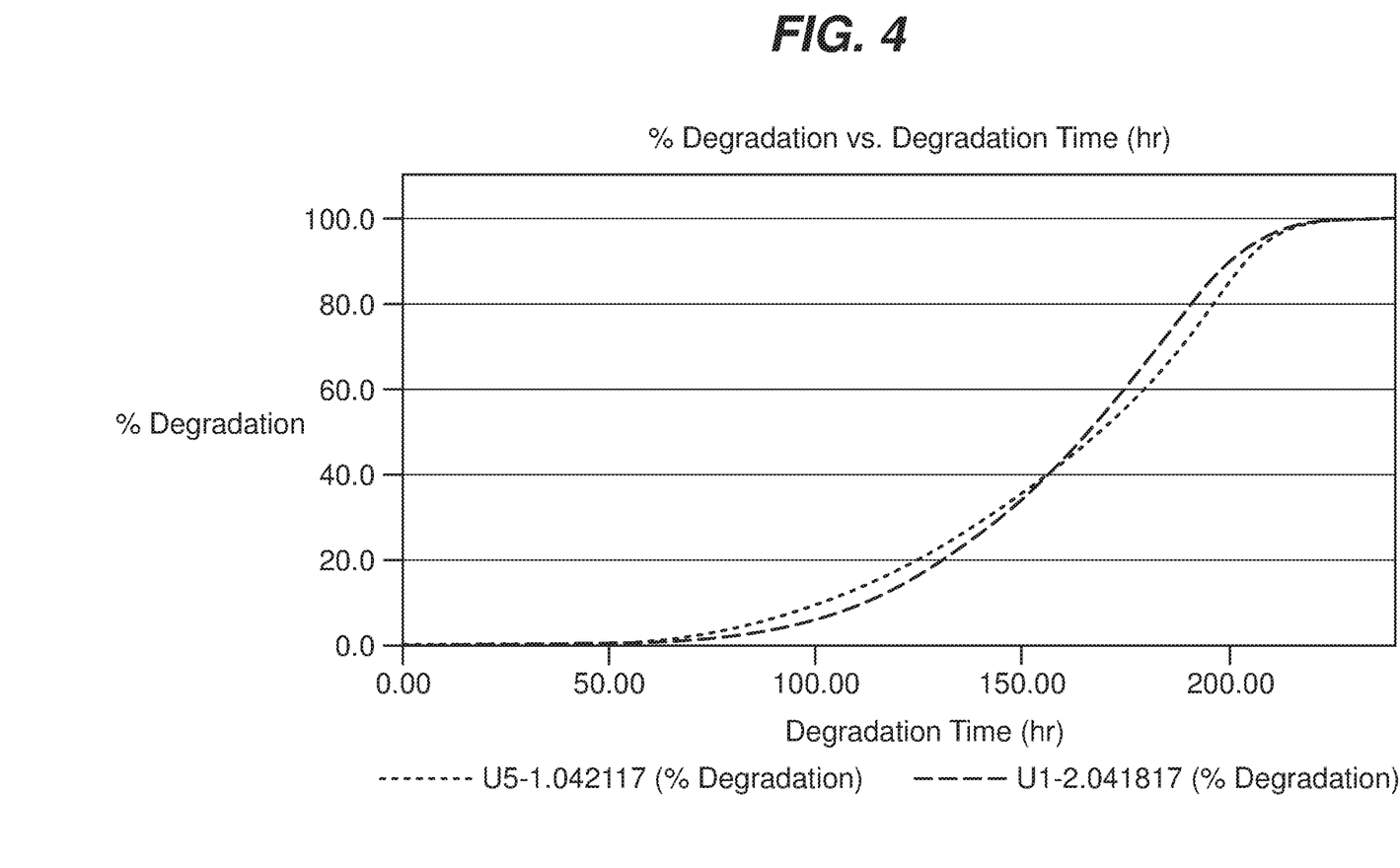
FIG. 4 is a graph showing two hydrolysis reactions (U5-11041117, U1-2041817) that were run on the same sample using the system of FIG. 3 with two different instruments setup; one with a FMI"Q" pump placed before the cooling device (U5-11041117) and another with Agilent HPLC pump placed after cooling device (U1-2041817).

The hydrolysis reaction was continuously monitored in the pH probe cell for pH changes (drops in pH) from the setpoint. If any decrease of pH was detected by Titrando, 0.05N sodium hydroxide solution was added into pH probe cell to return the pH to the setpoint automatically. The pH, temperature, and volume of 0.05N sodium hydroxide added to hydrolysis vessel were recorded by computer as a function of time. % degradation was calculated and plotted against time (FIG. 4). The results showed Pump position and type of pump used were not critical for the experiment as long as both burette and pH probe were place outside of reaction vessel.

% degradation=$V(t)/V(total)\times 100$

V(t)=NaOH volume used up to a timepoint; V(total)=total NaOH volume used.

The results showed, by placing the pH probe outside of reaction vessel in a cell and maintaining a, constant temperature of the bath flow in the cell, the hydrolysis profiles were significantly more repeatable and the data was significantly more reliable.

The novel methods and systems of the present invention have many advantages. The advantages include:

1. The in vitro degradation reaction can be carried out at high temperatures while the pH and progress of the degradation reaction can be monitored, adjusted, and recorded at ambient or reduced temperature
2. The lifespan of the pH probes can be significantly extended at reduced temperatures
3. The in vitro degradation profiles at accelerated conditions obtained by the new system are very reproducible, due to the more stable performance of the pH probes at lower temperature Although this invention has been shown and described with respect to detailed embodiments thereof, it will be understood by those skilled in the art that various changes in form and detail thereof may be made without departing from the spirit and scope of the claimed invention.

We claim:

1. A system for performing in vitro testing of bioabsorbable medical devices, comprising:
    a mixing reactor bath vessel for containing a bioabsorbable specimen and an aqueous bath, the bath vessel having an inlet and an outlet and a mixer;
    a thermocouple inserted into the bath vessel for measuring the temperature of the bath;
    a burette inserted into the bath vessel for delivering a flow of a base titrating solution;
    a circulation pump having an inlet and an outlet for cooling a first bath stream;
    a first pipe conduit for connecting the bath vessel outlet to an inlet of a circulation pump;
    a cooler having an inlet and an outlet for cooling the first bath stream;
    a second pipe conduit for connecting the outlet of the pump to the inlet of the cooler;
    a pH probe;
    a measuring vessel for holding the pH probe and receiving the cooled first bath stream, the vessel having an inlet and an outlet;
    a third pipe conduit for connecting the outlet of the cooler to the inlet of the measuring vessel;
    a fourth pipe conduit for connecting the outlet of the measuring vessel to the inlet of the bath vessel;
    a heat source associated with the bath vessel; and,
    a computer associated with the system to monitor, control, and record the temperature and pH of the aqueous bath and the flow of base titrating solution to the aqueous bath, and the temperature of the first bath stream exiting the cooler, as a function of time,
    wherein the first, second, third and fourth pipe conduit are in fluidic communication and the pH probe is arranged within the pH measuring vessel.

2. The system of claim 1, wherein the bioabsorbable specimen is selected from the group consisting of test coupons, sutures, tacks, meshes, staples, bone pins, bone plates, screws, ligating clips, staples, and knot clips.

3. The system of claim 1, wherein the bioabsorbable specimen comprises a bioabsorbable polymer.

4. The system of claim 3, wherein the bioabsorbable polymer is selected from the group consisting of aliphatic polyesters, poly(amino acids), copoly(ether-esters), polyalkylene oxalates, polyalkylene diglycolates, polyamides, tyrosine-derived polycarbonates, poly(iminocarbonates), polyorthoesters, polyoxaesters, polyamidoesters, polyoxaesters containing amine groups, poly(anhydrides), polyphosphazenes, poly(propylene fumarates), absorbable poly (ester urethanes), and combinations and blends thereof.

5. The system of claim 3, wherein the bioabsorbable polymer is a homopolymer or copolymer.

6. The system of claim 5, wherein the polymer comprises one or more of the monomers of lactic acid (including L-lactic acid and D-lactic acid), lactide (including L-, D-, meso and D,L-mixtures), glycolic acid, glycolide, ε-caprolactone, p-dioxanone (1,4-dioxan-2-one), trimethylene carbonate (1,3-dioxan-2-one), δ-valerolactone, ε-decalactone, 2,5-diketomorpholine (morpholinedione), pivalactone, diethylpropiolactone, ethylene carbonate, ethylene oxalate, 3-methyl-1,4-dioxane-2,5-dione, 3,3-diethyl-1,4,dioxan-2,5-dione, γ-butyrolactone, 1,4-dioxepan-2-one, 1,5-dioxepan-2-one, 6,6-dimethyl-dioxepan-2-one, 6,8-dioxabicycloctane-7-one or combinations thereof.

7. A system for performing in vitro testing of biodegradable medical devices, comprising:
    a mixing reactor bath vessel for containing a bioabsorbable medical device sample and an aqueous bath, the bath vessel having an inlet and an outlet and a mixer;
    a thermocouple inserted into the bath vessel for measuring the temperature of the bath;
    a circulation pump having an inlet and an outlet;
    a first pipe conduit for connecting the bath vessel outlet to an inlet of a circulation pump;
    a bath stream cooler having an inlet and an outlet for cooling a first bath stream;
    a second pipe conduit for connecting the outlet of the pump to the inlet of the cooler;
    a cell vessel having an inlet and an outlet;
    a burette inserted into the cell vessel for delivering a flow of base solution;
    a third pipe conduit for connecting the outlet of the cooler to the inlet of the cell vessel;
    a pH probe;
    a pH measuring vessel for holding the pH probe and for receiving the cooled first bath stream, the vessel having an inlet and an outlet, and a mixer;
    a fourth pipe conduit for connecting the outlet of the cell vessel to the inlet of the pH measuring vessel;
    a bath stream heater having an inlet and an outlet for heating the bath stream;
    a fifth pipe conduit for connecting the outlet of the pH measuring vessel; to the inlet of the heater;
    a sixth pipe conduit for connecting the outlet of the stream heater to the inlet of the reactor bath vessel;
    a heat source associated with the bath vessel; and,
    a computer associated with the system to monitor, control, and record the temperature and pH of the aqueous bath and the flow of base solution to the aqueous bath, and the temperatures of the first bath stream exiting the bath stream cooler and the bath stream heater, as a function of time,
    wherein the first, second, third, fourth, fifth and sixth pipe conduits are in fluidic communication and the pH probe is arranged within the pH measuring vessel.

8. The system of claim 7, wherein the bioabsorbable specimen is selected from the group consisting of test coupons, sutures, tacks, meshes, staples, bone pins, bone plates, screws, ligating clips, staples, and knot clips.

9. The system of claim 7, wherein the bioabsorbable specimen comprises a bioabsorbable polymer.

10. The system of claim 9, wherein the bioabsorbable polymer is selected from the group consisting of aliphatic polyesters, poly(amino acids), copoly(ether-esters), polyalkylene oxalates, polyalkylene diglycolates, polyamides, tyrosine-derived polycarbonates, poly(iminocarbonates), polyorthoesters, polyoxaesters, polyamidoesters, polyoxaesters containing amine groups, poly(anhydrides), polyphosphazenes, poly(propylene fumarates), absorbable poly (ester urethanes), and combinations and blends thereof.

11. The system of claim 9, wherein the bioabsorbable polymer is a homopolymer or copolymer.

12. The system of claim 11, wherein the polymer comprises one or more of the monomers of lactic acid (including L-lactic acid and D-lactic acid), lactide (including L-, D-, meso and D,L-mixtures), glycolic acid, glycolide, ε-caprolactone, p-dioxanone (1,4-dioxan-2-one), trimethylene carbonate (1,3-dioxan-2-one), δ-valerolactone, ε-decalactone, 2,5-diketomorpholine (morpholinedione), pivalactone, ☐,☐-diethylpropiolactone, ethylene carbonate, ethylene oxalate, 3-methyl-1,4-dioxane-2,5-dione, 3,3-diethyl-1,4,dioxan-2,5-dione, γ-butyrolactone, 1,4-dioxepan-2-one, 1,5-dioxepan-2-one, 6,6-dimethyl-dioxepan-2-one, 6,8-dioxabicycloctane-7-one or combinations thereof.

\* \* \* \* \*